United States Patent
Bedoukian

(10) Patent No.: US 9,924,718 B2
(45) Date of Patent: Mar. 27, 2018

(54) CONTROL AND REPELLENCY OF BITING FLIES, HOUSE FLIES, TICKS, ANTS, FLEAS, BITING MIDGES, COCKROACHES, SPIDERS AND STINK BUGS

(71) Applicant: Robert H. Bedoukian, West Redding, CT (US)

(72) Inventor: Robert H. Bedoukian, West Redding, CT (US)

(73) Assignee: Bedoukian Research, Inc., Danbury, CT (US)

( * ) Notice: Subject to any disclaimer, the term of this patent is extended or adjusted under 35 U.S.C. 154(b) by 0 days.

(21) Appl. No.: 13/998,326

(22) Filed: Oct. 21, 2013

(65) Prior Publication Data

US 2014/0323561 A1 Oct. 30, 2014

Related U.S. Application Data

(63) Continuation-in-part of application No. PCT/US2013/000123, filed on Apr. 30, 2013.

(51) Int. Cl.

| | | |
|---|---|---|
| *C07C 235/74* | (2006.01) | |
| *A01N 43/16* | (2006.01) | |
| *A01N 31/06* | (2006.01) | |
| *A01N 35/06* | (2006.01) | |
| *A01N 43/08* | (2006.01) | |
| *C07C 35/06* | (2006.01) | |
| *C07C 35/18* | (2006.01) | |
| *C07C 49/603* | (2006.01) | |
| *C07C 49/647* | (2006.01) | |
| *C07D 307/28* | (2006.01) | |
| *C07D 309/18* | (2006.01) | |
| *A01N 37/36* | (2006.01) | |
| *A01N 37/42* | (2006.01) | |

(52) U.S. Cl.
CPC .............. *A01N 43/16* (2013.01); *A01N 31/06* (2013.01); *A01N 35/06* (2013.01); *A01N 37/36* (2013.01); *A01N 37/42* (2013.01); *A01N 43/08* (2013.01); *C07C 35/06* (2013.01); *C07C 35/18* (2013.01); *C07C 49/603* (2013.01); *C07C 49/647* (2013.01); *C07C 235/74* (2013.01); *C07D 307/28* (2013.01); *C07D 309/18* (2013.01)

(58) Field of Classification Search
CPC .......... C07C 23/74; C07C 35/06; C07C 35/18
See application file for complete search history.

(56) References Cited

U.S. PATENT DOCUMENTS

| | | | |
|---|---|---|---|
| 4,332,941 A | 6/1982 | Berthold et al. | |
| 5,118,711 A | 6/1992 | Wilson et al. | |
| 6,060,507 A | 5/2000 | Hill et al. | |
| 7,622,498 B2 | 11/2009 | Justino et al. | |
| 9,339,030 B2 | 5/2016 | Burke et al. | |
| 2002/0193437 A1 | 12/2002 | Nagatsuka et al. | |
| 2004/0213822 A1 | 10/2004 | Birch et al. | |
| 2007/0196412 A1 | 8/2007 | Karl et al. | |
| 2008/0004339 A1 | 1/2008 | Justino et al. | |
| 2009/0082453 A1 | 3/2009 | Sheer et al. | |
| 2009/0099135 A1* | 4/2009 | Enan ...................... | A01N 65/00 514/86 |
| 2010/0179222 A1 | 7/2010 | Boulle et al. | |
| 2010/0278755 A1 | 11/2010 | Dell | |
| 2011/0124877 A1 | 5/2011 | Ito et al. | |
| 2011/0151248 A1 | 12/2011 | Buchotz et al. | |
| 2012/0046359 A1 | 2/2012 | Bedoukian | |
| 2012/0171313 A1 | 7/2012 | Boone | |

FOREIGN PATENT DOCUMENTS

| | | |
|---|---|---|
| JP | 63-048203 | 2/1988 |
| JP | 02-131405 | 5/1990 |
| JP | 04-164079 | 6/1992 |
| JP | H05140016 A | 6/1993 |
| JP | H05163182 A | 6/1993 |
| JP | H05163183 A | 6/1993 |
| JP | 05-178706 | 7/1993 |
| JP | H05208902 A | 8/1993 |
| JP | H05213802 A | 8/1993 |
| JP | 07-138102 | 5/1995 |
| JP | 2002-356404 | 12/2002 |
| JP | 2003238388 A | 8/2003 |

(Continued)

OTHER PUBLICATIONS

Brown et al 'Insect repellants: An overview' Journal of the American Academy of Dermatology, 36(2), p. 243-249, 1997.*

(Continued)

*Primary Examiner* — Craig D Ricci
*Assistant Examiner* — Christopher R Stone
(74) *Attorney, Agent, or Firm* — Ohlandt, Greenley, Ruggiero & Perle, L.L.P.

(57) ABSTRACT

Control and repellency of biting flies, house flies, ticks, ants, fleas, biting midges, cockroaches, spiders and stink bugs is obtained by contact of the insects with at least one of the compounds of the structure (I).

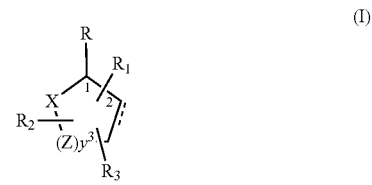

25 Claims, No Drawings

(56) References Cited

FOREIGN PATENT DOCUMENTS

| | | |
|---|---|---|
| JP | 2005-162730 | 6/2005 |
| JP | 2007-502860 | 2/2007 |
| JP | 2009-256311 | 11/2009 |
| JP | 2009-542789 | 12/2009 |
| JP | 2013503169 A | 1/2013 |
| JP | 2013-126960 | 6/2013 |
| WO | 2004-100971 A1 | 11/2004 |
| WO | 2008007100 A2 | 1/2008 |
| WO | 2010126576 A1 | 11/2010 |
| WO | 2011151248 A1 | 8/2011 |
| WO | 2012047608 A2 | 4/2012 |
| WO | 2013050967 A1 | 4/2013 |
| WO | 2013165475 A1 | 11/2013 |
| WO | 2013165478 A1 | 11/2013 |
| WO | 2014028835 A2 | 2/2014 |
| WO | 2014031790 A1 | 2/2014 |
| WO | 2014099821 A2 | 6/2014 |

OTHER PUBLICATIONS

Taylor et al 'Structure-Activity Relationship of a Broad-Spectrum Insect Odorant Receptor Agonist' ACS Chemical Biology, vol. 7, p. 1647-1652, 2012.*

International Preliminary Report on Patentability dated Nov. 13, 2014 from corresponding application PCT/US2013/000123, 11 pages.

International Search Report dated Jun. 23, 2015, from corresponding PCT Application No. PCT/US14/61579 , 6 pages.

International Written Opinion dated Jun. 23, 2015, from corresponding PCT Application No. PCT/US14/61579 , 5 pages.

Chinese First Office Action dated Oct. 9, 2015 in corresponding Chinese Application No. 201380022885.9 with English translation, 20 pages.

Extended European Search Report dated Feb. 9, 2016 from corresponding EP Application No. 13785212.5, 15 pages.

Japanese Office Action dated Feb. 23, 2016 from corresponding Japanese Application No. JP2015-510251, 10 pages.

European Search Report dated Nov. 16, 2015 from corresponding European Patent Application No. 13785212.5, 7 pages.

Japanese Notification of Reasons for Refusal dated Jan. 10, 2017 from corresponding Japanese Patent Application No. 2015-510251, 11 pages.

European Examination Search Report dated Nov. 16, 2016 from corresponding EP Application No. 13785212.5, 2 pages.

Chinese Office Action dated Nov. 10, 2016 from corresponding Chinese Patent Application No. 201380022885.9, 9 pages.

EP examination report for EP application 13 785 212.5, dated Jun. 8, 2017, 7 pages.

Japanese Office Action for corresponding Japanese Application JP2016-549219, dated Jun. 29, 2017, 8 pages.

* cited by examiner

CONTROL AND REPELLENCY OF BITING FLIES, HOUSE FLIES, TICKS, ANTS, FLEAS, BITING MIDGES, COCKROACHES, SPIDERS AND STINK BUGS

RELATED APPLICATIONS

This Application is a continuation-in-part of Patent Application No. PCT/US2013/00123, filed Apr. 30, 2013, claiming priority from U.S. Provisional Patent Application No. 61/687,917, filed May 2, 2012.

FIELD OF THE INVENTION

This invention relates to compounds used as agents to control and repel biting flies, house flies, ticks, ants, fleas, biting midges, cockroaches, spiders and stink bugs.

BACKGROUND TO THE INVENTION

It is known that insects and others pests have plagued humankind since the beginning of human existence and a wide variety of control agents and insecticides and pesticides have been employed for the purpose of attempting to control, repel or eradicate such insects and pests. However most of these agents are difficult to apply or pose dangers to both humans and the environment. DDT, which was commonly used in World War II and thereafter, has been banned because of safety concerns. A common component in many presently used chemical insecticides is pyrethrin which, while considered amongst the safest insecticides, is known to irritate eyes, skin, and respiratory systems in humans. In addition, pyrethrin is known to be particularly harmful to aquatic life.

DEET®, namely N,N-Diethyl-m-toluamide, is widely used against a variety of insects and pests, but is characterized by an unseemly bad smell, is not particularly long lasting in its effect and it dissolves plastics. Moreover, several safety questions have been raised concerning the use of DEET® and some governments have restricted the amount of the active component that may be employed in formulations. This itself presents a further problem since DEET® is subject to evaporation and it needs to be formulated at higher than effective dosages in order to maintain its effectiveness. Furthermore, many insects and pests have developed resistance to DEET® due to its wide spread usage.

As such, there is a need to provide an insect or pest repellent formulation which is non-toxic to the people, plants, and other animals which may be exposed to areas of application. A further need is for a pest or insect control formulation that comprises long lasting effects, thereby limiting the need for frequent re-application to treated areas. A further need is for such a pest or insect control formulation that may be toxic to certain pests or insects but not to humans and that do not produce an undesirable effect on the environment.

SUMMARY OF THE INVENTION

In accordance with this invention, control and repellency of biting flies, house flies, ticks, ants, fleas, biting midges, cockroaches, spiders and stink bugs is obtained by contact of the insects with at least one of the compounds of the structure (I)

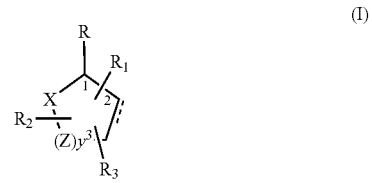

wherein
R is selected from —OH, =O, —OC(O)$R_4$, —$OR_6$, and —$(OR_6)_2$, wherein each $R_6$ is independently selected from an alkyl group containing from 1 to 4 carbon atoms and $R_4$ is a branched or straight chain, saturated or unsaturated, hydrocarbyl group with zero to two double bonds and from 1 to 15 carbon atoms;
X is O or $CH_2$, with the proviso that when X is OR can only be =O;
each Z is independently selected from (CH) and ($CH_2$);
y is a numeral selected from 1 and 2;
$R_1$ is selected from H or a branched or straight chain, saturated or unsaturated hydrocarbyl group with zero to two double bonds and from 1 to 15 carbon atoms;
$R_2$ is selected from H and a branched or straight chain, saturated or unsaturated hydrocarbyl group with zero to three double bonds and from 1 to 15 carbon atoms;
$R_3$ is selected from H, a branched or straight chain, saturated or unsaturated hydrocarbyl group with zero to three double bonds and from 1 to 15 carbon atoms, —$(CH_2)_n$OH, —C(O)$OR_5$, —$CH_2$C(O)$OR_7$, —$CH_2$C(O)$R_8$, —C(O)$NR_9R_{10}$, and —$CH_2$C(O)$NR_{11}R_{12}$ where each of $R_5$, $R_7$, $R_8$, $R_9$, $R_{10}$, $R_{11}$ and $R_{12}$ is independently selected from H and a branched or straight chain, saturated or unsaturated hydrocarbyl group with zero to three double bonds and from 1 to 15 carbon atoms, and n is n integer of from 1 to 12;
the bond between the 2 and 3 positions in the ring structure may be a single or a double bond; and
wherein the compounds of structure (I) contain from 11 to 20 carbon atoms except where R is =O, X=$CH_2$ and y is 1 the compounds of structure (I) contain from 13 to 20 carbon atoms, with the proviso that when $R_3$ is —$CH_2$C(O)$OR_7$, $R_1$ and $R_2$ must be H or a saturated hydrocarbyl group with zero double bonds. The invention also includes optical isomers, diastereomers and enantiomers of the compounds of structure (I). Thus, at all stereocenters where stereochemistry is not explicitly defined, all possible epimers are envisioned.

The compounds of structure (I) may be employed to control biting flies, house flies, ticks, ants, fleas, biting midges, cockroaches, spiders and stink bugs. The compounds of structure (I) have been found to be toxic to ticks and roaches and may be used successfully to kill these an other insects by applying the compounds to areas or environments where they are known to or suspected to inhabit. For purposes of obtaining toxicity it is preferred that the compounds of structure (I) contain from 11 to 17 carbon atoms and more preferably contain from 11 to 14 carbon atoms. The compounds of structure (I) may be employed in any suitable formulation, such as for example as solutions, oils, creams, lotions, aerosols or the like. Formulations may be employed in the form of cleaning products, wipes, etc. and applied to either skin or inanimate surfaces. The compounds of this invention are long lasting and do not require frequent reapplication.

DETAILED DESCRIPTION OF THE INVENTION

Control and repellency of biting flies, house flies, ticks, ants, fleas, biting midges, cockroaches, spiders and stink bugs is obtained by contact of the insects with at least one of the compounds of the structure (I)

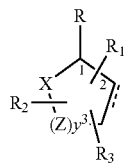
(I)

wherein
R is selected from —OH, =O, —OC(O)R$_4$, —OR$_6$, and —(OR$_6$)$_2$, wherein each R$_6$ is independently selected from an alkyl group containing from 1 to 4 carbon atoms and R$_4$ is a branched or straight chain, saturated or unsaturated hydrocarbyl group with zero to two double bonds and from 1 to 15 carbon atoms;
X is O or CH$_2$, with the proviso that when X is OR can only be =O;
each Z is independently selected from (CH) and (CH$_2$);
y is a numeral selected from 1 and 2;
R$_1$ is selected from H or a branched or straight chain, saturated or unsaturated hydrocarbyl group with zero to two double bonds and from 1 to 15 carbon atoms;
R$_2$ is selected from H and a branched or straight chain, saturated or unsaturated hydrocarbyl group with zero to three double bonds and from 1 to 15 carbon atoms;
R$_3$ is selected from H, a branched or straight chain, saturated or unsaturated hydrocarbyl group with zero to three double bonds and from 1 to 15 carbon atoms, —(CH$_2$)$_n$OH, —C(O)OR$_5$, —CH$_2$C(O)OR$_7$, —CH$_2$C(O)R$_8$, —C(O)NR$_9$R$_{10}$, and —CH$_2$C(O)NR$_{11}$R$_{12}$ where each of R$_5$, R$_7$, R$_8$, R$_9$, R$_{10}$, R$_{11}$ and R$_{12}$ is independently selected from H and a branched or straight chain, saturated or unsaturated hydrocarbyl group with zero to three double bonds and from 1 to 15 carbon atoms, and n is n integer of from 1 to 12;
the bond between the 2 and 3 positions in the ring structure may be a single or a double bond; and
wherein the compounds of structure (I) contain from 11 to 20 carbon atoms except where R is =O, X=CH$_2$ and y is 1 the compounds of structure (I) contain from 13 to 20 carbon atoms, with the proviso that when R$_3$ is —CH$_2$C(O)OR$_7$, R$_1$ and R$_2$ must be H or a saturated hydrocarbyl group with zero double bonds. The invention also includes optical isomers, diastereomers and enantiomers of the named structures. Thus, at all stereocenters where stereochemistry is not explicitly defined, all possible epimers are envisioned. For purposes of obtaining toxicity it is preferred that the compounds of structure (I) contain from 11 to 17 carbon atoms and more preferably contain from 11 to 14 carbon atoms.

A preferred group of control and repellency compounds are those compounds of Structure (I) wherein
R is selected from —OH and =O, X is CH$_2$, y is 1 or 2, each Z is selected from (CH) and (CH$_2$), the bond between positions 2 and 3 in the ring is a single bond, one of R$_1$ and R$_2$ is H or —CH$_3$ and the other of R$_1$ and R$_2$ is a branched or straight chain, saturated or unsaturated hydrocarbyl group containing from 9 to 15 carbon atoms and 0 to 3 double bonds, and R$_3$ is H.

Another preferred group of control and repellency compounds are those compounds of structure (I) wherein
R is selected from —OH and =O, more preferably =O, X is CH$_2$, y is 1 or 2, more preferably 1, each Z is selected from (CH) and (CH$_2$), the bond between positions 2 and 3 in the ring is a single or double bond, more preferably a single bond, one of R$_1$ and R$_2$ is H and the other of R$_1$ and R$_2$ is a branched or straight chain, saturated or unsaturated hydrocarbyl group containing from 9 to 15 carbon atoms and 0 to 3 double bonds, and R$_3$ is selected from —C(O)OR$_5$ and —CH$_2$C(O)R$_8$ where R$_5$ and R$_8$ are each selected from a straight chain or branched, saturated or unsaturated hydrocarbyl group containing from 1 to 6 carbon atoms, and more preferably 3 to 5 carbon atoms and still more preferably —CH$_3$.

Another preferred group of control and repellency compounds are those compounds of structure (I) wherein
R is =O, X is O, y is 1 or 2, each Z is selected from (CH) and (CH$_2$), the bond between positions 2 and 3 of the rings is a single or double bond, more preferably a single bond, one of R$_1$ and R$_2$ is H and the other of R$_1$ and R$_2$ is a branched or straight chain, saturated or unsaturated hydrocarbyl group containing from 9 to 15 carbon atoms and 0 to 3 double bonds, and R$_3$ is selected from —C(O)OR$_5$ and —CH$_2$C(O)R$_8$ where R$_5$ and R$_7$ are each selected from a hydrocarbyl group containing from 1 to 6 carbon atoms, and more preferably 3 to 5 carbon atoms and still more preferably —CH$_3$ and wherein the total number of carbon atoms in the compounds of structure (I) is from 11 to 17, more preferably from 11 to 14 total carbon atoms.

Another preferred group of control and repellency compounds are those compounds of structure (I) wherein
R is =O, X is O, y is 1 or 2, each Z is selected from (CH) and (CH$_2$), the bond between positions 2 and 3 in the ring is a single bond, R$_1$ is a branched or straight chain, saturated or unsaturated alkyl group containing from 5 to 13 carbon atoms, R$_2$ is H or —CH$_3$, R$_3$ is H, and more preferably where R$_1$ is an alkyl group of from 5 to 10 carbon atoms such that the compound of structure (I) contains from 11 to 14 total carbon atoms.

Another preferred group of control and repellency compounds are those compounds of structure (I) wherein
the at least one compound of the structure (1) is a compound selected from a compound of structure (1) wherein R$_1$—OH and =O, R$_1$ and R$_2$ are each selected from H or a saturated hydrocarbyl group with zero double bonds, X is O, Z is selected from (CH) and (CH$_2$), y is 1, the bond between positions 2 and 3 of the rings is a single bond, R$_3$ is —CH$_2$C(O)OR$_7$, and R$_7$ is selected from H and a branched or straight chain, saturated or unsaturated hydrocarbyl group with zero or 1 double bonds and containing from 1 to 15 carbon atoms.

The active compounds of structure (I) may be formulated into any suitable formulations such as for example, including but not limited to, solutions, oils, creams, lotions, shampoos, aerosols or the like. Traditional inert carriers such as, including but not limited to, alcohols, esters and petroleum distillates, could be used to produce formulations of the active compounds to be used as repellent formulations. Another series of carriers include but are not limited to the biodegradable oils, including the Olestra® family of oils, isopropyl myristate and squalane.

When the formulation will be used as an aerosol, it is preferable to add a propellant. Suitable propellants include propane, butane, isobutane, dimethyl ether, carbon dioxide, nitrous oxide, nitrogen, and combinations thereof.

The formulations described above can be prepared by any convenient means, e.g., by mixing the active compound or active compounds with one or more other ingredients described above. In addition, active components of structure (I) may be blended with existing active repellents or toxicants including, but not limited to, N,N-Diethyl-m-toluamide (DEET®) and p-Menthane-3,8-diol (PMD).

Representative examples of compounds of structure (I) include, but are not limited to,

methyl 2-(3-oxo-2-pentylcyclopentyl)acetate
Chemical Formula: $C_{13}H_{22}O_3$
Molecular Weight: 226.31
Methyl Dihydro Jasmonate

methyl 2-(3-hydroxy-2-pentylcyclopentyl)acetate
Chemical Formula: $C_{13}H_{24}O_3$
Molecular Weight: 228.33
Methyl Dihydro Jasmolate

ethyl 2-(3-oxo-2-pentylcyclopentyl)acetate
Chemical Formula: $C_{14}H_{24}O_3$
Molecular Weight: 240.34
Ethyl Dihydro Jasmonate

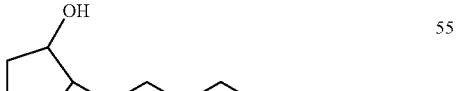

ethyl 2-(3-hydroxy-2-pentylcyclopentyl)acetate
Chemical Formula: $C_{14}H_{26}O_3$
Molecular Weight: 242.35
Ethyl Dihydro Jasmolate

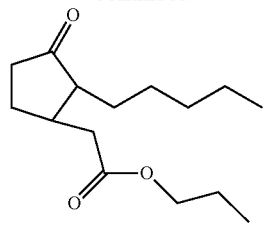

propyl 2-(3-oxo-2-pentylcyclopentyl)acetate
Chemical Formula: $C_{15}H_{26}O_3$
Molecular Weight: 254.37
Propyl Dihydro Jasmonate

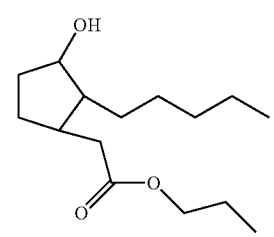

propyl 2-(3-hydroxy-2-pentylcyclopentyl)acetate
Chemical Formula: $C_{15}H_{28}O_3$
Molecular Weight: 256.38
Propyl Dihydro Jasmolate

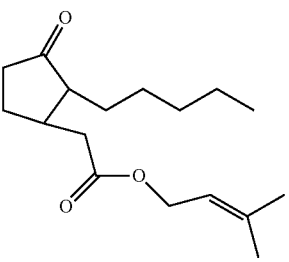

3-methylbut-2-enyl 2-(3-oxo-2-pentylcyclopentyl)acetate
Chemical Formula: $C_{17}H_{28}O_3$
Molecular Weight: 280.40
Prenyl Dihydro Jasmonate

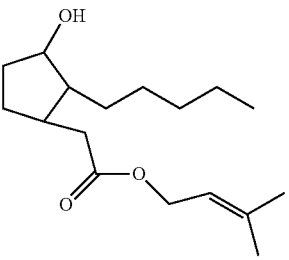

3-methylbut-2-enyl 2-(3-hydroxy-2-pentylcyclopentyl)acetate
Chemical Formula: $C_{17}H_{30}O_3$
Molecular Weight: 282.42
Prenyl Dihydro Jasmolate -continued

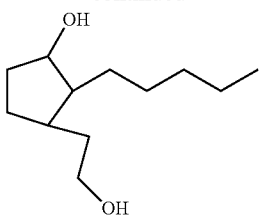

3-(2-hydroxyethyl)-2-pentylcyclopentanol
Chemical Formula: $C_{12}H_{24}O_2$
Molecular Weight: 200.32
MethylDihydroJasmodiol

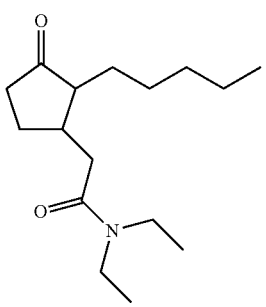

N,N-diethyl-2-(3-oxo-2-pentylcyclopentyl)acetamide
Chemical Formula: $C_{16}H_{29}NO_2$
Molecular Weight: 267.41
MDJ Amide

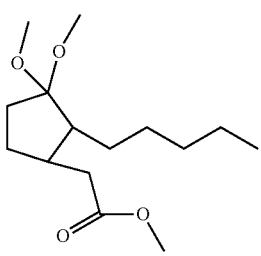

methyl 2-(3,3-dimethoxy-2-pentylcyclopentyl)acetate
Chemical Formula: $C_{15}H_{28}O_4$
Molecular Weight: 272.38
Methyl Dihydro Jasmonate Dimethyl Ketal

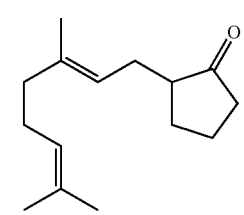

(E)-2-(3,7-dimethylocta-2,6-dienyl)cyclopentanone
Chemical Formula: $C_{15}H_{24}O$
Molecular Weight: 220.35
Apritone -continued

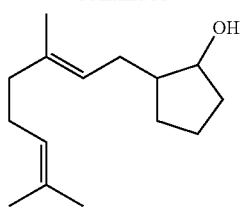

(E)-2-(3,7-dimethylocta-2,6-dienyl)cyclopentanol
Chemical Formula: $C_{15}H_{26}O$
Molecular Weight: 222.37
Apritol

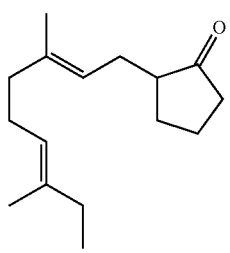

2-((2E,6E)-3,7-dimethylnona-2,6-dienyl)cyclopentanone
Chemical Formula: $C_{16}H_{26}O$
Molecular Weight: 234.38
Methyl Apritone

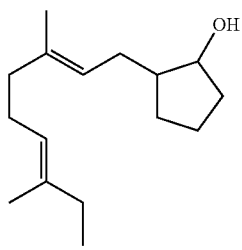

2-((2E,6E)-3,7-dimethylnona-2,6-dienyl)cyclopentanol
Chemical Formula: $C_{16}H_{28}O$
Molecular Weight: 236.39
Methyl Apritol

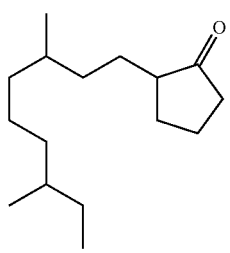

2-(3,7-dimethylnonyl)cyclopentanone
Chemical Formula: $C_{16}H_{30}O$
Molecular Weight: 238.41
Tetrahydromethyl Apritone -continued

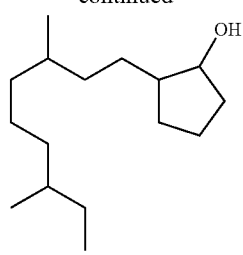

2-(3,7-dimethylnonyl)cyclopentanol
Chemical Formula: C$_{16}$H$_{32}$O
Molecular Weight: 240.42
Tetrahydromethyl Apritol

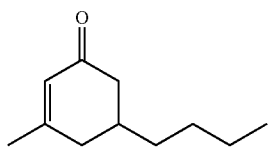

Chemical Formula: C11H18O
Molecular Weight: 166.26
3-methyl-5-butyl-2-cyclohexenone

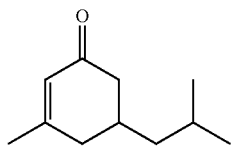

Chemical Formula: C11H18O
Molecular Weight: 166.26
3-methyl-5-isobutyl-2-cyclohexenone

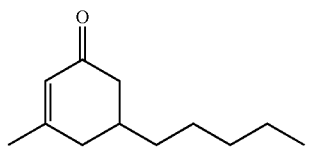

Chemical Formula: C12H20O
Molecular Weight: 180.29
3-methyl-5-pentyl-2-cyclohexenone

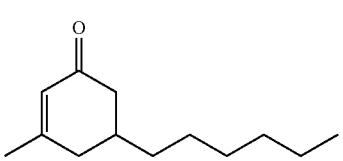

Chemical Formula: C13H22O
Molecular Weight: 194.31
3-methyl-5-hexyl-2-cyclohexenone

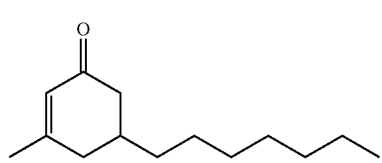

Chemical Formula: C14H24O
Molecular Weight: 208.34
3-methyl-5-heptyl-2-cyclohexenone -continued

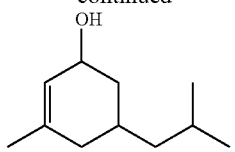

Chemical Formula: C11H20O
Molecular Weight: 168.28
3-methyl-5-isobutyl-2-cyclohexen-1-ol

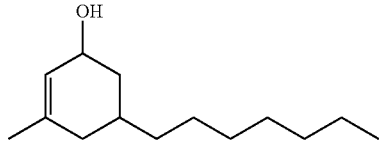

3-methyl-5-heptyl-2-cyclohexen-1-ol
Chemical Formula: C14H26O
Molecular Weight: 210.36

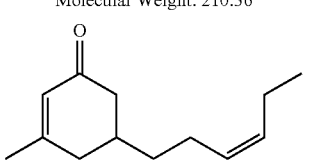

Chemical Formula: C13H20O
Molecular Weight: 192.30
3-methyl-5-(z-3-hexenyl)-2-cyclohexenone

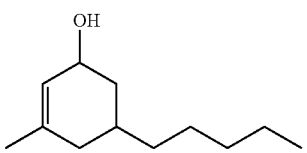

3-methyl-5-pentyl-2-cyclohexen-1-ol
Chemical Formula: C12H22O
Molecular Weight: 182.30

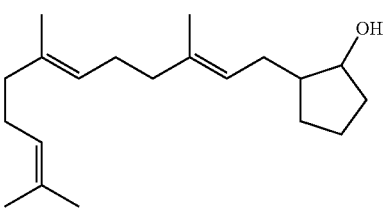

2-((2E,6E)-3,7,11-trimethyldodeca-2,6,10-trienyl)cyclopentanol
Chemical Formula: C$_{20}$H$_{34}$O
Molecular Weight: 290.48
Farnesylcyclopentanol

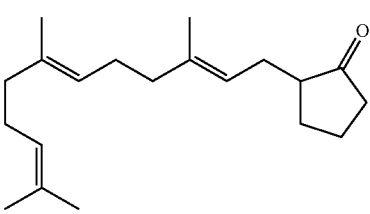

2-((2E,6E)-3,7,11-trimethyldodeca-2,6,10-trienyl)cyclopentanone
Chemical Formula: C$_{20}$H$_{32}$O
Molecular Weight: 288.47
Farnesylcyclopentanone -continued

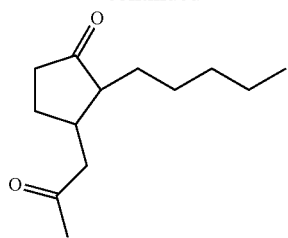

3-(2-oxopropyl)-2-pentylcyclopentanone
Chemical Formula: $C_{13}H_{22}O_2$
Molecular Weight: 210.31
Amyl Cyclopentanone Propanone

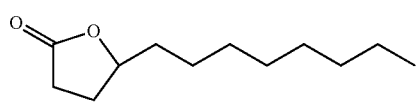

5-octyldihydrofuran-2(3H)-one
Chemical Formula: $C_{12}H_{22}O_2$
Molecular Weight: 198.30
gamma-dodecalactone

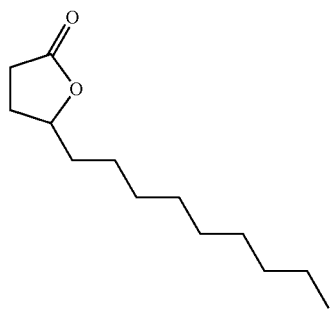

5-nonyldihydrofuran-2(3H)-one
Chemical Formula: $C_{13}H_{24}O_2$
Molecular Weight: 212.33
Gamma-Tridecalactone

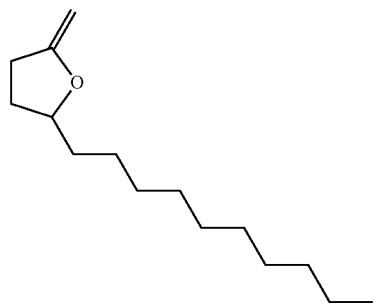

5-decyldihydrofuran-2(3H)-one
Chemical Formula: $C_{14}H_{26}O_2$
Molecular Weight: 226.36
Gamma-Tetradecalactone

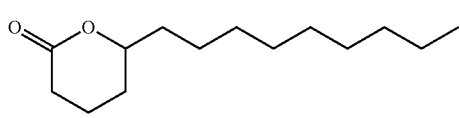

6-nonyltetrahydro-2H-pyran-2-one
Chemical Formula: $C_{14}H_{26}O_2$
Molecular Weight: 226.36
Delta-Tetradecalactone -continued

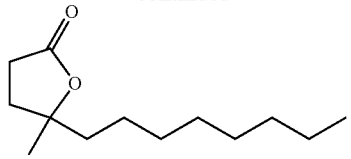

Gamma Methyl Dodecalactone
2(3H)-Furanone, 5-octyldihydro-5-methyl-

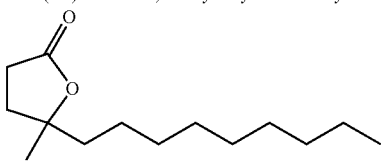

Gamma Methyl Tridecalactone
5-methyl-5-nonyldihydrofuran-2(3H)-one
4-methyl-4-nonyl gamma butyrolactone
C14 lactone

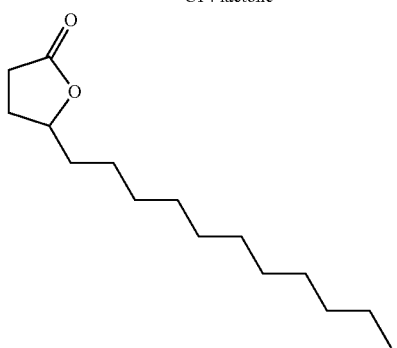

Chemical Formula: $C_{15}H_{28}O_2$
Molecular Weight: 240.38
Gamma Pentadecalactone and

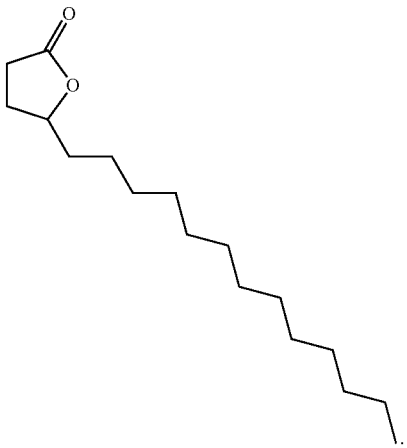

gamma Heptadecalactone
Chemical Formula: $C_{17}H_{32}O_2$
Molecular Weight: 268.24

Especially preferred compounds of structure (I) include methyl apritone, methyl dihydrojasmonate, propyl dihydrojasmonate, gamma-dodecalactone, gamma-tridecalactone, gamma-tetradecalactone, gamma methyl dodecalactone, gamma methyl tridecalactone, 3-methyl-5-pentyl-2-cyclohexenone, 3-methyl-5-pentyl-2-cyclohexenol and 3-methyl-5-heptyl-2-cyclohexenone.

The active control agents of this invention are an effective control agent against biting flies, house flies, ticks, ants, fleas, biting midges, cockroaches, spiders and stink bugs.

Biting flies include but are not limited to sand flies, stable flies, deer flies, horse flies, black flies and biting midges. House flies include but are not limited to common house flies and lesser house flies. Examples of ticks include but are not limited to deer ticks, lone star ticks and brown dog ticks. Ants include but are not limited to carpenter ants, bullet ants, Jack jumper ants, Pharaoh ants and fire ants. Cockroaches include but are not limited to American cockroaches, German cockroaches, Oriental cockroaches and tropical cockroaches. Spiders include, but are not limited to, cob-web spinning spiders like the Black Widow. Stink bugs include but are not limited to the Brown Marmorated Stink Bug, Southern Green Stink Bug, Forest Bug, Harlequin Bug and the Rice Stink Bug.

The amount of active compound of structure (I) utilized in any control or repellent formulation will depend upon the type of formulation used and the insect or pest against which the formulation is employed but will generally range from about 1% to about 30% by weight in an inert carrier.

The active control compounds of structure (I) may be applied to surfaces of or impregnated in clothing or fabric. The amount of active material can be about 0.025 g/ft$^2$ to about 3.6 g/ft$^2$. When the compounds of structure (I) are employed as toxicants for ticks the compound will be applied to an area or environment so as to provide from about 0.025 g/ft$^2$ to about 4.79 g/ft$^2$ of an area or environment where the toxic effect on the ticks is desired.

The invention is illustrated by, but not limited to, the following examples.

Control against sand flies was determined by the following protocol as generally described in J. Med. Entomol. 43 (6), 1248-1252 (2006). Volunteers wearing short pants were seated. Using a skin-marking template and a washable-ink marker, skin areas represented by 3- by 4-cm floor opening of six cells of a K&D module were outlined on the outer, top and inner thigh position of each leg of the volunteers. The six treated cell rectangles each represented a random block, and each volunteer had three blocks on each of two thighs. All treatments against the sand flies *P. papatasi*, were pipetted onto a 4- by 5-cm rectangular area (so the area of skin covered by a treatment exceeded the template marks by 0.5 cm in every direction) of the subjects' skin with 55 ul of isopropyl alcohol/treatment containing 10% or 5% compound/ul isopropyl alcohol. Treating a slightly larger area ensured that the areas beneath each K&D module contained only treated skin. Skin treated with isopropyl alcohol alone served as control. In all tests adjacent cells of the K&D module were supplied with ten sand flies. The sand fly charged K&D module was positioned over the treated skin areas and the trap doors of the K&D module above the areas were opened. After a five minute skin exposure the trap doors were closed. The number of sand fly bites was recorded for each cell. The data for this test is presented in Table 1. The percent biting is the percent compared to the biting for the control which was taken as 100%.

TABLE 1

| Compound | Treatment level-10% | Treatment level 5% |
| --- | --- | --- |
| Isopropyl alcohol (control) | 100% | 100% |
| Methyl apritone | 0% | 9.9% |
| Methyl apritol | 0% | 12.5% |
| Methyl dihydrojasmonate | — | 0% |
| Methyl dihydrojasmolate | 0% | 0% |

At a concentration of 10% there is complete repellency for all compounds tested. At 5%, methyl dihydrojasmonate and methyl dihydrojasmolate still repelled 100% of the sand flies, while methyl apritone and methyl apritol repelled 90.1% and 87.5% respectively.

The following test protocol was employed to demonstrate the efficacy of compounds of this invention to control or repel stable flies. Five replicates of 100 mixed-sex stable flies each were placed in screened cages. The cages were placed in such a way that the stable flies had access to five warmed, blood-filled membrane walls. The membranes were treated with methyl dihydrojasmonate, gamma-dodecalactone, methyl apritone, or DEET® all at 7% and at 15% in isopropyl alcohol, or isopropyl alcohol as a control. There were five replicates tested with a positional rotation of the repellent at each replicate. Fresh batches of stable flies were used for each replicate. Thus each test sample was tested on each of the five wells, which allowed any positional bias to be eliminated. The number of stable flies probing each well was recorded at two minute intervals for twenty minutes. The total number of probes on each well were tallied at the end of the twenty minute observation period and the average percentage repellency was calculated for each compound. An analysis of variance was conducted to compare the average number of probes on each treatment membrane. The number of probes for the control was taken as the 100% baseline and the percentage for the test compounds is the percent for the number of probes for the test compound compared to the number of control probes. The results are set forth in Table 2.

TABLE 2

| Test Compound | Probes at 7% test compound | Probes at 15% test compound |
| --- | --- | --- |
| Isopropyl alcohol (control) | 100% | 100% |
| DEET® | 45.9% | 16.2% |
| Methyl apritone | 28.8% | 7.4% |
| Methyl dihydrojasmonate | 4.5% | 3.2% |
| Gamma dodecalactone | 6.2% | 3.6% |

As shown in the table above, all treated membranes repelled vs. the control. Methyl apritone, methyl dihydrojasmonate and γ-dodecalactone each repelled better than DEET® at the same concentrations.

Human testing was also performed to demonstrate the effectiveness of our repellents against stable flies. Tests were also performed with compounds from Structure (I) in combination with para-menthane-3,8-diol (PMD) to demonstrate synergistic effects. Two insect repellents per day were tested by applying one on each arm of a human subject and inserting the arms into a cage containing 50 stable flies. The exposure period was five minutes at every 30 minute interval until the first time a confirmed bite was sust5 The stable flies were reared at ambient temperature, relative humidity and photoperiod. Groups of 50 flies were aspirated from the cage and released into 16 oz. cups with screened lids, which were used to release flies into the two test cages. The test subjects had a 250 cm$^2$ area on each forearm measured and marked for treatment. Adjacent areas above and below the treated area were protected with elastic bandages held in place with Elastikon® surgical tape.

The application rate was between 0.65 ml and 1 ml/250 cm$^2$ for all repellents. The actual amount of repellent used was based upon the amount that provides thorough coverage of the 250 cm$^2$ treatment area. A repellent was applied using either a micropipette or a syringe minus the needle. The repellents were then evenly spread on the treatment area with a gloved finger. Each test subject's forearms were allowed to air dry for approximately 30 minutes prior to the first exposure. The study coordinator or technician assisted the test subjects in inserting their arms into the test cages, taking care not to rub them on the cloth sleeve. Both treated arms were inserted into a cage; there were two subjects (4 arms) per cage. The test subjects exposed their treated forearms to the flies in the test cages for 5 minutes. The subjects then removed their arms from the cages with assistance from the study coordinator or a technician. Exposures of each arm were repeated every 30 minutes until the repellent on that arm was determined to be no longer effective ('breakdown') or until 8 hours have elapsed, whichever occurs first.

Breakdown occurs when the first confirmed bite is noted. A confirmed bite occurs when a bite is followed by a second bite in the same exposure period or in the next succeeding exposure period. The second bite becomes the confirming bite and the breakdown time is taken as the time of the first bite. When a confirmed bite occurs, testing is discontinued on that arm. Results in Table 3 below are the average of two trials on two different test subjects. Compounds were diluted in isopropyl alcohol.

TABLE 3

| Compound | 100% bite protection for |
|---|---|
| 15% p-Menthane-3,8-diol (PMD) | 4.25 hr |
| 30% PMD | 6.5 hr |
| 30% Propyl Dihydrojasmonate (PDJ) | 4 hr |
| 15% PMD AND 15% PDJ | 8 hr |
| 30% gamma Methyl tridecalatcone | 1.75 hr |
| 15% PMD AND 15% gamma Tridecalactone | 6.25 hr |

As shown in the table above, when combined with known repellents, like PMD, our materials show a synergistic effect.

To demonstrate the effectiveness of our compounds against house flies, three replicates of 50 house flies were released into 1×1×1 ft. screened cages. The bottom of each cage was lined with brown craft paper and divided into 4 equal quadrants. Each quadrant housed a makeshift filter paper food tray. Two of the four filter papers were treated with repellent and two treated with isopropanol. Control cages contained filter papers that were treated with 4 filter papers of isopropanol only. The number of flies resting on filter paper per quadrant was recorded every 30 minutes for a total of 6 hours. Cages were rotated to eliminate positional bias. Table 4 below shows the overall repellency of the compounds tested. Each of the test samples were diluted in isopropyl alcohol.

TABLE 4

| Test Sample in isopropyl alcohol | Overall % Repellency |
|---|---|
| 5% Methyl Dihydrojasmonate | 52 |
| 5% Propyl Dihydrojasmonate | 52 |
| 7.5% Propyl Dihydrojasmonate | 23 |
| 5% Methyl Apritone | 45 |
| 5% gamma Tridecalactone | 80 |
| 5% delta Tetradecalactone | 76 |
| 7.5% gamma Dodecalactone | 100 |
| 7.5% gamma Tridecalactone | 94 |
| 7.5% gamma Tetradecalactone | 80 |
| 7.5% gamma Pentadecalactone | 87 |
| 7.5% gamma Heptadecalactone | 39 |

Control against Brown Dog ticks was determined in the following protocol. Strips of filter paper, 1" by 3", were placed on a sheet of aluminum foil treated with 1 ml each of the test samples and allowed to dry. The end of each treated strip was stapled to an untreated filter paper strip of the same dimensions. The stapled strips were suspended in a vertical position above a tray, with the treated half attached to a horizontal glass rod by a metal clip. The untreated half was lowered when the strip is vertically positioned. Brown Dog Ticks, *Rhipicephalus sanguineus*, mixed sexes, were purchased from a supplier. Five replicates of five ticks for each treatment regimen plus five additional replicates for the control were employed. Ticks shipped to the test site were given at least one day to acclimate to "shipping stress" before they are used for testing. Those tick specimens which appeared sluggish or moribund were not used. Suitable ticks were removed from their containers and allowed to quest on the free end of the test strip. Once present on the strip they were watched as they crawled up the strip until they contacted the treated paper. If the tick, once in contact with the treated zone, either turned around, stopped without proceeding further, or dropped off, the tick is classified as repelled. If it continued to crawl onto the treated strip, even after it stopped briefly, that tick was classified as not repelled. A maximum observation time of 1 minute per replicate was allowed for ticks to respond after reaching the treated area, but during the test, if more time was needed, the maximum observation time may have been adjusted at the discretion of the study coordinator. At the end of the observation time, the number of ticks repelled was recorded. Tick behavior was recorded when applicable, such as whether increased number of affected or repelled ticks occurred in successive replicates over time. After the completion of each treatment parameter, the testing chamber was ventilated for five minutes by turning on the exhaust fan and opening the door leading into the chamber. Ticks were used only once. Average number of ticks displaying each behavior category were calculated and compared to the control replicates.

As shown below in Table 5, in this test protocol the control with no repellent repelled 0% of the ticks. γ-dodecalactone, methyl apritone and methyl dihydro jasmonate each repelled 100% of the ticks.

TABLE 5

| Treatment in isopropyl alcohol unless otherwise noted | Mean % repelled |
|---|---|
| Control | 0 |
| gamma-Dodecalactone (Neat) | 100 |
| Gamma Tridecalactone (7.5%) | 100 |
| Methyl apritone (Neat) | 100 |
| Methyl apritone (7.5%) | 100 |
| Methyl dihydrojasmonate (Neat) | 100 |
| 7.5% Propyl dihydrojasmonate (PDJ) | 96 |
| 7.5% PDJ/PMD* at 52:48 ratio | 100 |

*PMD = p-Menthane-3,8-Diol

Also, a second repellent assay was used to evaluate six test samples against Brown Dog Ticks. Five replicates of five ticks were given the opportunity to quest onto a vertical strip of untreated filter paper and then allowed to move upward toward a second vertical strip of filter paper treated with one of the six candidate repellents or DEET®. In the control situation, the second strip was treated with isopropanol. They were then observed for directional or behavioral changes caused in response to contact with the repellent. Ticks were recorded as either repelled or not repelled. Compounds were diluted in isopropyl alcohol. The percentages of ticks repelled are shown below in Table 6.

TABLE 6

| Treatment | Mean % Repelled |
| --- | --- |
| Control | 4 |
| gamma-Tetradecalactone (15%) | 92 |
| Methyl dihydrojasmonate (15%) | 100 |
| Propyl dihydrojasmonate (15%) | 100 |
| Methyl apritone (15%) | 100 |
| DEET (7%) | 96 |

The following protocol was employed to test compounds of this invention for toxicity (mortality) against ticks. There were 5 replicates of 5 dog ticks for each treatment. Five replicates of 5 ticks did not receive any treatment and served as controls. Filter paper strips were laid on a sheet of aluminum foil and enough of each of the test sample was applied to thoroughly saturate the paper. The paper was then rolled and placed inside a glass shell vial as to line the sides of the vial. A small paper disc, also saturated with the test sample, was then placed at the bottom of the vial. Brown Dog Ticks, *Rhipicephalus sanguineus*, were then introduced into the vials which were covered with aluminum foil, the inside of which was painted with some of the test sample. The ticks remained in the vials, constantly exposed to the test samples, for the duration of the test. A small hole was poked through the foil for ventilation. Each control replicate was subjected to the same procedures outlined above, except that they were not treated. The controls were placed in the same area as the test replicates for the duration of the test. Mortality observations were made at 24 hours. Ticks were classified as alive (able to move normally), moribund (those classified as moribund will show some movement, but will not be able to crawl in a coordinated manner, or will be unable to right themselves if placed on their backs), or dead (no movement after physical stimuli). All dead ticks were confirmed by probing or agitation to make sure that they are unable to move; any that show movement visible to the naked eye were recorded as moribund. At 24 hours the tick mortality was 0% for the control, 100% for γ-dodecalactone, 100% for methyl apritone and 76% for methyl dihydrojasmonate. See Table 7 for tabulated results.

TABLE 7

| Treatment | 24 hr mortality (%) |
| --- | --- |
| Control | 0 |
| gamma-Dodecalactone (neat) | 100 |
| Methyl apritone (neat) | 100 |
| Methyl dihydrojasmonate (neat) | 76 |
| 3-Methyl-5-Pentyl-2-cyclohexenol (10%) | 12 (100% morbidity) |

Pharaoh ants were tested using the following protocol. The side of a 17"×23" rectangular sheet of poster board was sprayed with the test sample or acetone, except for a region within a 6" circle. The treated poster board was allowed to dry. Five worker ants were placed in the center of the 6" untreated circle and allowed to wander outside the circle onto the treated surface. The behavior of the ants at the treated-untreated interface was recorded for 5 minutes after release. Test compounds were diluted in acetone.

TABLE 8

| Test Compound | % crossed without stopping | % stopped at interface | % slowed, but crossed |
| --- | --- | --- | --- |
| Acetone (control) | 82 | 12 | 4 |
| Methyl dihydrojasmonate (50%) | 50 | 32 | 20 |
| Methyl apritone (50%) | 66 | 66 | 2 |
| Gamma Dodecalactone (50%) | 82 | 10 | 8 |

The efficacy of compounds of this invention to control or repel German cockroaches was illustrated using the following protocol. One food pellet each was placed on a paper square (station) treated with one of the repellent materials. Materials were diluted to 50% in acetone and a straight acetone station was also used. Both stations were placed on the same side of the arena. Cockroaches were starved for 2 days and then released into the arena. They were given a choice to feed on either food pellet. A control arena with an acetone treated station and an untreated station was also used. The distribution of cockroaches within the arena was recorded at 30 minute intervals over 4 hours. Repellency at 4 hours was calculated by the number of cockroaches on the untreated station vs. the total number of cockroaches on the stations. It excludes those roaches that did not feed. Table 9 demonstrates these results.

TABLE 9

| Treatment in acetone | % Repellency 4 hr |
| --- | --- |
| Methyl apritone (50%) | 100 |
| Methyl dihydrojasmonate (50%) | 72.2 |
| Propyl dihydrojasmonate (50%) | 87.5 |
| Prenyl dihydrojasmonate (50%) | 87.5 |
| Farnesyl cyclopentanone (50%) | 100 |
| gamma-Dodecalactone (50%) | 96.6 |
| gamma-Tetradecalactone (50%) | 82.4 |
| gamma-Tetradecalactone (50%) | 75 |
| gamma-Heptadecalactone (50%) | 100 |

Additionally, toxicity was determined by forced exposure testing under the following protocol. Filter paper circles were treated with test compound. Cockroaches were released onto the treated circles and covered with inverted plastic cylinders placed over the paper discs. The cockroaches were left on the substrates for 24 hours and checked for mortality.

TABLE 10

| Compound in acetone unless otherwise noted | Mortality @ 24 hours |
| --- | --- |
| gamma-Heptadecalactone (neat) | 22% |
| gamma-Tetradecalactone (neat) | 46% |
| 3-Methyl-5-pentyl-2-cyclohexenone (2.5%) | 96% |
| 3-Methyl-5-heptyl-2-cyclohexenone (2.5%) | 10% |

Control against Black Widow spiders was determined using the following protocol. One test container containing two card stock tube shelters, one half treated with a test sample and the other half treated with isopropanol was prepared. A spider was introduced in the center of the tube. The spider was then given a choice to move to one end of the shelters. The following day, its location is recorded and compared to the results from a shelter containing untreated half-shelters.

On the day of the test one of the two shelters was sprayed with the test sample solution using a 2 oz pump spray bottle.

Only the surfaces that the spider will most likely contact were treated. Therefore, only the inside of one of the shelter tubes, including the end disc (spiders will not be able to access the outside part of the shelter) were sprayed. The total amount of product was weighed and recorded. The treated surface was allowed to dry for a minimum of ½ hour, or until solvent could not be detected by smell. At this time the shelter tubes were assembled.

Card stock paper tube shelters were constructed from 2 half-letter sized sheets (5½"×8½") of paper, rolled and taped together to form a short tube. One end of each was covered with a circle of card stock paper, while the other end was later taped to the open end of the other half sheet, forming one long tube. Each paper circle had a hole punched in the center for viewing and the circle was held in place with the transparent plastic wrapping and tape and/or rubber bands. The solvent-treated half was labeled with a "C" on the inner and outer walls with a pencil or a pen with solvent resistant ink. Prior to forming the final tube shelter, a semi-circular hole was cut into one of the margins of each sheet such that, once the two tubes are taped together, the holes correspond to the top and at the junction of the tubes for introduction of the spiders.

Twenty-five arenas were prepared in this manner for each test sample. There were five replicates of five spiders. Twenty-five additional control arenas were also prepared. They were prepared the same way, except that areas to be sprayed were sprayed with isopropanol only.

Replicates of five spiders were selected for each test formulation and for the control. The specimens were visually examined for overall physical condition. Unresponsive spiders or specimens which exhibited uncoordinated movement prior to test start were rejected. The spiders were transferred directly into the holding vials using flexible forceps or with a little coaxing with an artist brush. Because of their cannibalistic tendencies, each vial contained only one spider. There they were held until the time for testing.

At the test start the spiders were placed directly in the middle, through the opening at the top of the shelter tube, and the opening covered, with only one spider per arena. After this introduction the spiders' movement was watched for a short time to observe whether spiders exhibited signs of extensive agitation or morbidity from exposure to the test samples. They were left alone for 24 hours, after which time their location within the arena was recorded. Spiders present inside the shelter treated with the test repellent were considered tolerant.

Distribution results are summarized below in Table 11.

TABLE 11

| Compound @ 5% in isopropanol | % Repellency |
|---|---|
| Methyl dihydrojasmonate | 87.5 |
| Propyl dihydrojasmonate | 62.5 |
| Methyl apritone | 37.5 |
| gamma Tridecalactone | 75.0 |
| gamma Pentadecalactone | 75.0 |

To demonstrate repellency of our materials against brown marmorated stink bugs (BMSB), five replicate arenas were set up each with two semi-circle filter papers (one treated and one untreated.) A treated semi-circle filter paper was placed on the bottom of each test arena next to an untreated half semi-circle filter paper. The two semi-circle filter papers were aligned together to completely cover the bottom of the test arena. Control arenas were also set up in a similar fashion except both were treated with acetone. Five replicates of 5 BMSB were then introduced into both the treated and control arenas. By releasing them in the center of the arena, the BMSB were presented with a choice of treated vs. untreated substrate (or untreated vs. untreated in the control arenas). The repellency of the BMSB was recorded at 24 hours post-treatment. Results are summarized below in Table 12.

TABLE 12

| Formulations in isopropyl alcohol | % Repellency at 24 hours |
|---|---|
| Methyl dihydrojasmonate (2.5%) | 74 |
| Methyl dihydrojasmonate (5%) | 100 |
| Propyl dihydrojasmonate (2.5%) | 80 |
| Propyl dihydrojasmonate (5%) | 100 |
| gamma-Dodecalactone (10%) | 100 |
| gamma-Tridecalactone (5%) | 70 |
| gamma-Methyl tridecalactone (2.5%) | 80 |
| gamma-Tetradecalactone (2.5%) | 82 |
| gamma-Tetradecalactone (5%) | 91 |
| p-Menthane-3,8-diol (2.5%) | 80 |

While the invention has been described herein with reference to the specific embodiments thereof, it will be appreciated that changes, modification and variations can be made without departing from the spirit and scope of the inventive concept disclosed herein. Accordingly, it is intended to embrace all such changes, modification and variations that fall with the spirit and scope of the appended claims.

I claim:

1. A method for the control or repellency of one or more of insects selected from the group of biting flies, house flies, ticks, ants, fleas, biting midges, cockroaches, spiders and stink bugs, the method comprising bringing the insects into contact with an inhibitory effective amount of at least one of the compounds selected from the group consisting of

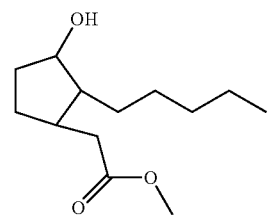

methyl 2-(3-hydroxy-2-pentylcyclopentyl)acetate
Chemical Formula: $C_{13}H_{24}O_3$
Molecular Weight: 228.33
Methyl Dihydro Jasmolate

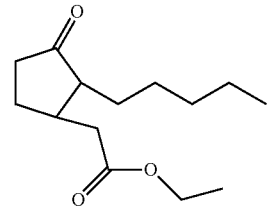

ethyl 2-(3-oxo-2-pentylcyclopentyl)acetate
Chemical Formula: $C_{14}H_{24}O_3$
Molecular Weight: 240.34
Ethyl Dihydro Jasmonate

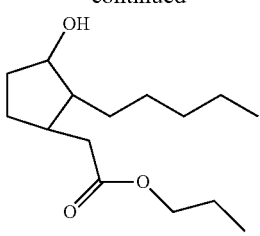

propyl 2-(3-hydroxy-2-pentylcyclopentyl)acetate
Chemical Formula: $C_{15}H_{28}O_3$
Molecular Weight: 256.38
Propyl Dihydro Jasmolate

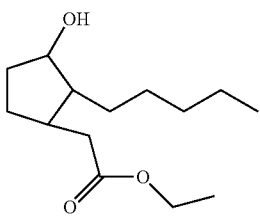

ethyl 2-(3-hydroxy-2-pentylcyclopentyl)acetate
Chemical Formula: $C_{14}H_{26}O_3$
Molecular Weight: 242.35
Ethyl Dihydro Jasmolate

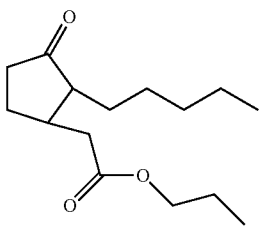

propyl 2-(3-oxo-2-pentylcyclopentyl)acetate
Chemical Formula: $C_{15}H_{26}O_3$
Molecular Weight: 254.37
Propyl Dihydro Jasmonate

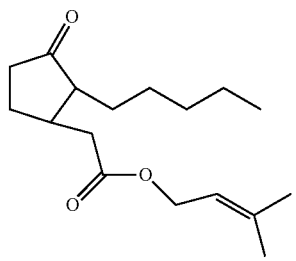

3-methylbut-2-enyl 2-(3-oxo-2-pentylcyclopentyl)acetate
Chemical Formula: $C_{17}H_{28}O_3$
Molecular Weight: 280.40
Prenyl Dihydro Jasmonate

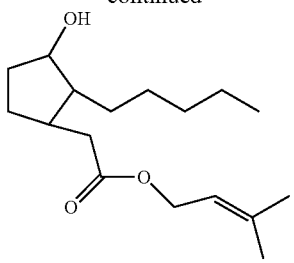

3-methylbut-2-enyl 2-(3-hydroxy-2-pentylcyclopentyl)acetate
Chemical Formula: $C_{17}H_{30}O_3$
Molecular Weight: 282.42
Prenyl Dihydro Jasmolate

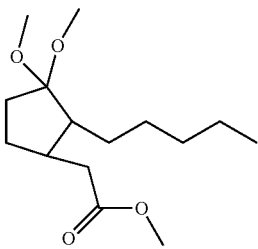

methyl 2-(3,3-dimethoxy-2-pentylcyclopentyl)acetate
Chemical Formula: $C_{15}H_{28}O_4$
Molecular Weight: 272.38
Methyl Dihydro Jasmonate Dimethyl Ketal

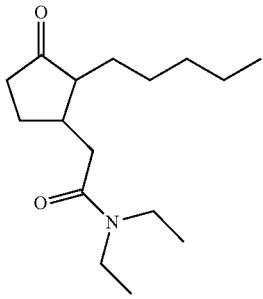

and

N,N-diethyl-2-(3-oxo-2-pentylcyclopentyl)acetamide
Chemical Formula: $C_{16}H_{29}NO_2$
Molecular Weight: 267.41
MDJ Amide

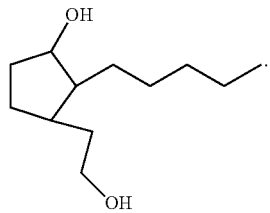

3-(2-hydroxyethyl)-2-pentylcyclopentanol
Chemical Formula: $C_{12}H_{24}O_2$
Molecular Weight: 200.32
MethylDihydroJasmodiol 2. A method for the control or repellency of one or more of insects selected from the group of biting flies, house flies, ticks, ants, fleas, biting midges, cockroaches, spiders and stink bugs, the method comprising bringing the insects into contact with an inhibitory effective amount of at least one of the compounds selected from the group consisting of:

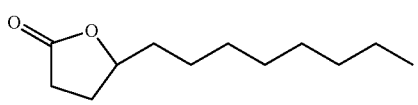

5-octyldihydrofuran-2(3H)-one
Chemical Formula: $C_{12}H_{22}O_2$
Molecular Weight: 198.30
gamma-dodecalactone

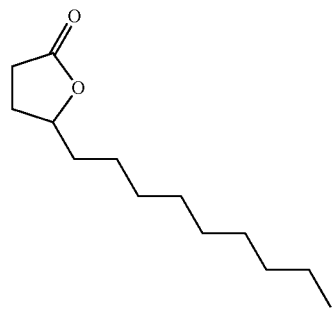

5-nonyldihydrofuran-2(3H)-one
Chemical Formula: $C_{13}H_{24}O_2$
Molecular Weight: 212.33
Gamma-Tridecalactone

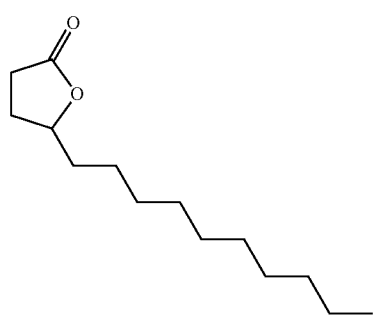

5-decyldihydrofuran-2(3H)-one
Chemical Formula: $C_{14}H_{26}O_2$
Molecular Weight: 226.36
Gamma-Tetradecalactone

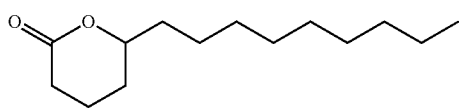

6-nonyltetrahydro-2H-pyran-2-one
Chemical Formula: $C_{14}H_{26}O_2$
Molecular Weight: 226.36
Delta-Tetradecalactone

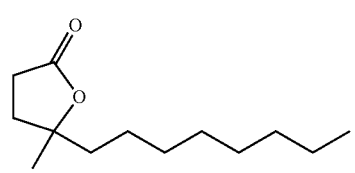

Gamma Methyl Dodecalactone
2(3H)-Furanone, 5-octyldihydro-5-methyl-

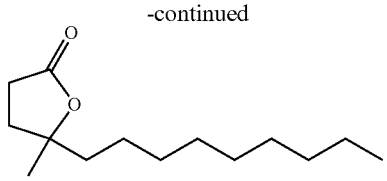

Gamma Methyl Tridecalactone
5-methyl-5-nonyldihydrofuran-2(3H)-one
4-methyl-4-nonyl gamma butyrolactone
C14 lactone

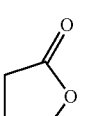

Chemical Formula: $C_{15}H_{28}O_2$
Molecular Weight: 240.38
Gamma Pentadecalactone and

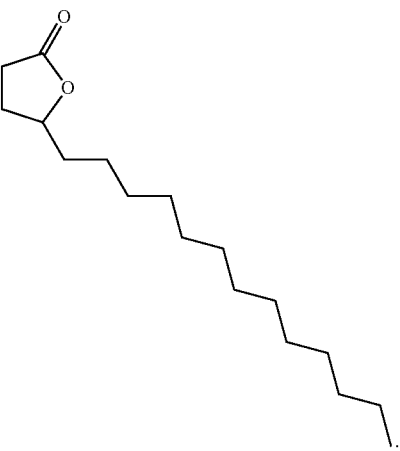

gamma Heptadecalactone
Chemical Formula: $C_{17}H_{32}O_2$
Molecular Weight: 268.24

3. A method for the control or repellency of one or more of insects selected from the group of biting flies, house flies, ticks, ants, fleas, biting midges, cockroaches, spiders and stink bugs, the method comprising bringing the insects into contact with an inhibitory effective amount of at least one of the compounds selected from the group consisting of:

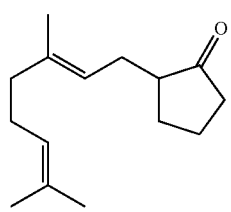

(E)-2-(3,7-dimethylocta-2,6-dienyl)cyclopentanone
Chemical Formula: $C_{15}H_{24}O$
Molecular Weight: 220.35
Apritone

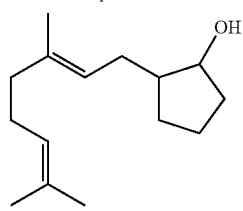

(E)-2-(3,7-dimethylocta-2,6-dienyl)cyclopentanol
Chemical Formula: $C_{15}H_{26}O$
Molecular Weight: 222.37
Apritol

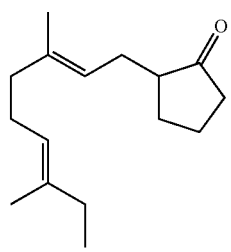

2-((2E,6E)-3,7-dimethylnona-2,6-dienyl)cyclopentanone
Chemical Formula: $C_{16}H_{26}O$
Molecular Weight: 234.38
Methyl Apritone

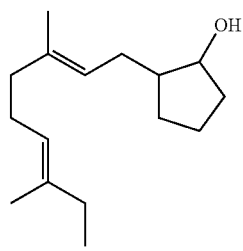

2-((2E,6E)-3,7-dimethylnona-2,6-dienyl)cyclopentanol
Chemical Formula: $C_{16}H_{28}O$
Molecular Weight: 236.39
Methyl Apritol

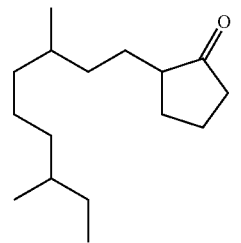

and 2-(3,7-dimethylnonyl)cyclopentanone
Chemical Formula: $C_{16}H_{30}O$
Molecular Weight: 238.41
Tetrahydromethyl Apritone -continued

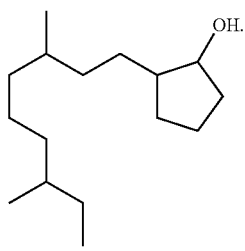

2-(3,7-dimethylnonyl)cyclopentanol
Chemical Formula: $C_{16}H_{32}O$
Molecular Weight: 240.42
Tetrahydromethyl Apritol 4. A method for the control or repellency of one or more of insects selected from the group of biting flies, house flies, ticks, ants, fleas, biting midges, cockroaches, spiders and stink bugs, the method comprising bringing the insects into contact with an inhibitory effective amount of at least one of the compounds selected from the group consisting of:

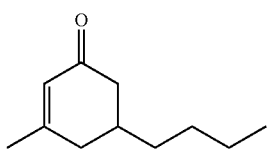

Chemical Formula: C11H18O
Molecular Weight: 166.26
3-methyl-5-butyl-2-cyclohexenone

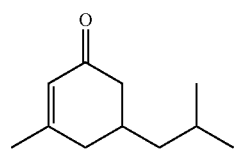

Chemical Formula: C11H18O
Molecular Weight: 166.26
3-methyl-5-isobutyl-2-cyclohexenone

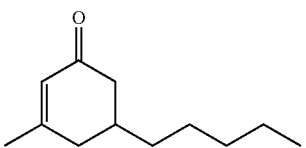

Chemical Formula: C12H20O
Molecular Weight: 180.29
3-methyl-5-pentyl-2-cyclohexenone

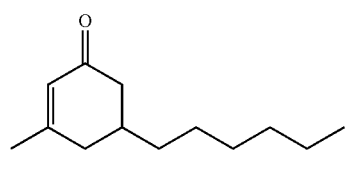

Chemical Formula: C13H22O
Molecular Weight: 194.31
3-methyl-5-hexyl-2-cyclohexenone -continued

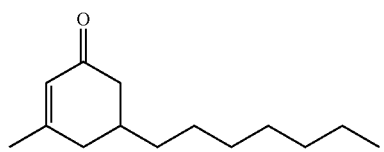

Chemical Formula: C14H24O
Molecular Weight: 208.34
3-methyl-5-heptyl-2-cyclohexenone

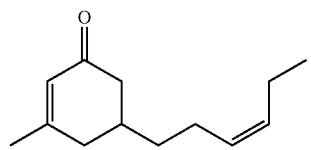

Chemical Formula: C13H20O
Molecular Weight: 192.30
3-methyl-5-(z-3-hexenyl)-2-cyclohexenone

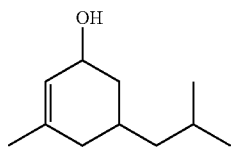

Chemical Formula: C11H20O
Molecular Weight: 168.28
3-methyl-5-isobutyl-2-cyclohexen-1-ol

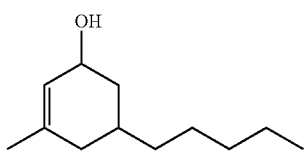

3-methyl-5-pentyl-2-cyclohexen-1-ol
Chemical Formula: C12H22O
Molecular Weight: 182.30

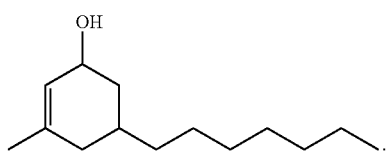

3-methyl-5-heptyl-2-cyclohexen-1-ol
Chemical Formula: C14H26O
Molecular Weight: 210.36

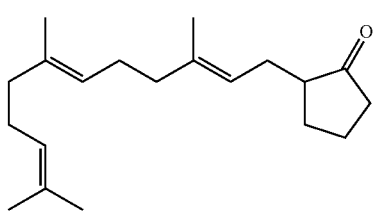

2-((2E,6E)-3,7,11-trimethyldodeca-2,6,10-trienyl)cyclopentanone
Chemical Formula: C20H32O
Molecular Weight: 288.47
Farnesylcyclopentanone -continued

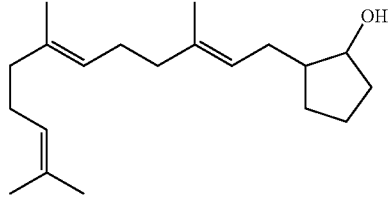

2-((2E,6E)-3,7,11-trimethyldodeca-2,6,10-trienyl)cyclopentanol
Chemical Formula: C20H34O
Molecular Weight: 290.48
Farnesylcyclopentanol

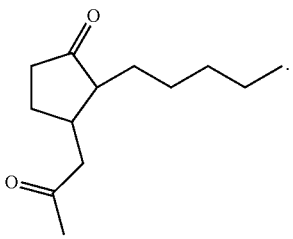

3-(2-oxopropyl)-2-pentylcyclopentanone
Chemical Formula: C13H22O2
Molecular Weight: 210.31
Amyl Cyclopentanone Propanone 5. A method for the control or repellency of one or more of insects selected from the group of biting flies, house flies, ticks, ants, fleas, biting midges, cockroaches, spiders and stink bugs, the method comprising bringing the insects into contact with an inhibitory effective amount of at least one of the compounds is selected from methyl apritone, propyl dihydrojasmonate, gamma-dodecalactone, gamma-tridecalactone, gamma-tetradecalactone, gamma methyl dodecalactone and gamma methyl tridecalactone, 3-methyl-5-pentyl-2-cyclohexenone, 3-methyl-5-pentyl-2-cyclohexenol and 3-methyl-5-heptyl-2-cyclohexenone.

6. The method of claim 1 wherein the at least one of the compounds is applied to the skin in the form of wipes, lotions, creams, oils, or sprays.

7. The method of claim 1 wherein the at least one of the compounds in combination with a compound selected from DEET® (N,N-Diethyl-m-toluamide) and para-menthane-3,8-diol is applied to the skin in the form of wipes, lotions, creams, oils, or sprays.

8. The method of claim 1 wherein the at least one of the compounds is applied to a surface of or impregnated into clothing or fabric, or is applied to cleaning products.

9. The method of claim 1 wherein the contacting of ticks or roaches with the at least one of the compounds produces toxicity to the ticks or roaches.

10. The method of claim 2 wherein the at least one of the compounds is applied to the skin in the form of wipes, lotions, creams, oils, or sprays.

11. The method of claim 2 wherein the at least one of the compounds in combination with a compound selected from DEET® (N,N-Diethyl-m-toluamide) and para-menthane-3,8-diol is applied to the skin in the form of wipes, lotions, creams, oils, or sprays.

12. The method of claim 2 wherein the at least one of the compounds is applied to a surface of or impregnated into clothing or fabric, or is applied to cleaning products.

13. The method of claim 2 wherein the contacting of ticks or roaches with the at least one of the compounds produces toxicity to the ticks or roaches.

14. The method of claim 3 wherein the at least one of the compounds is applied to the skin in the form of wipes, lotions, creams, oils, or sprays.

15. The method of claim 3 wherein the at least one of the compounds in combination with a compound selected from DEET® (N,N-Diethyl-m-toluamide) and para-menthane-3,8-diol is applied to the skin in the form of wipes, lotions, creams, oils, or sprays.

16. The method of claim 3 wherein the at least one of the compounds is applied to a surface of or impregnated into clothing or fabric, or is applied to cleaning products.

17. The method of claim 3 wherein the contacting of ticks or roaches with the at least one of the compounds produces toxicity to the ticks or roaches.

18. The method of claim 4 wherein the at least one of the compounds is applied to the skin in the form of wipes, lotions, creams, oils, or sprays.

19. The method of claim 4 wherein the at least one of the compounds in combination with a compound selected from DEET® (N,N-Diethyl-m-toluamide) and para-menthane-3,8-diol is applied to the skin in the form of wipes, lotions, creams, oils, or sprays.

20. The method of claim 4 wherein the at least one of the compounds is applied to a surface of or impregnated into clothing or fabric, or is applied to cleaning products.

21. The method of claim 4 wherein the contacting of ticks or roaches with the at least one of the compounds produces toxicity to the ticks or roaches.

22. The method of claim 5 wherein the at least one of the compounds is applied to the skin in the form of wipes, lotions, creams, oils, or sprays.

23. The method of claim 5 wherein the at least one of the compounds in combination with a compound selected from DEET® (N,N-Diethyl-m-toluamide) and para-menthane-3,8-diol is applied to the skin in the form of wipes, lotions, creams, oils, or sprays.

24. The method of claim 5 wherein the at least one of the compounds is applied to a surface of or impregnated into clothing or fabric, or is applied to cleaning products.

25. The method of claim 5 wherein the contacting of ticks or roaches with the at least one of the compounds produces toxicity to the ticks or roaches.

\* \* \* \* \*